United States Patent [19]

Hirose et al.

[11] Patent Number: 4,709,088
[45] Date of Patent: Nov. 24, 1987

[54] PROCESS FOR PRODUCING 2,6-NAPHTHALENE-DICARBOXYLIC ACID

[75] Inventors: Isao Hirose; Tamio Amemiya; Tokuji Sakai, all of Matsuyama, Japan

[73] Assignee: Teijin Petrochemical Industries, Ltd., Tokyo, Japan

[21] Appl. No.: 883,479

[22] Filed: Jul. 15, 1986

Related U.S. Application Data

[63] Continuation of Ser. No. 664,049, Oct. 23, 1984, abandoned.

[30] Foreign Application Priority Data

Oct. 24, 1983 [JP]  Japan ................................. 58-197558
Oct. 24, 1983 [JP]  Japan ................................. 58-197559

[51] Int. Cl.[4] ................... C07C 51/265; C07C 51/16; C07C 51/23
[52] U.S. Cl. .................................... 562/414; 562/408; 562/416; 562/418; 562/421; 568/321; 568/432; 568/565; 568/808
[58] Field of Search ............... 562/414, 416, 421, 488; 568/321, 432, 565, 808

[56] References Cited

U.S. PATENT DOCUMENTS 3,870,754  3/1975  Yamashita et al. ................. 562/416
3,970,696  7/1976  Shigeyasu et al. .................. 562/414
4,314,073  2/1982  Crooks ............................... 562/416

Primary Examiner—Donald B. Moyer
Assistant Examiner—Patricia M. Scott
Attorney, Agent, or Firm—Sherman and Shalloway

[57] ABSTRACT

A process for producing 2,6-naphthalenedicarboxylic acid which comprises oxidizing 2,6-diisopropylnaphthalene or its oxidation product as a starting material with molecular oxygen in a reaction medium containing at least 50% by weight of an aliphatic monocarboxylic acid having not more than 3 carbon atoms in the presence of an oxidation catalyst comprising (A) at least one heavy metal element selected from the group consisting of cobalt and manganese, and (B) bromine element, the 2,6-diisopropylnaphthalene and/or its oxidation product being used in a proportion of 0.1 to 5 moles per gram-atom of the heavy metal element of the oxidation catalyst.

12 Claims, No Drawings

PROCESS FOR PRODUCING 2,6-NAPHTHALENE-DICARBOXYLIC ACID

This application is a continuation of application Ser. No. 664,049, filed Oct. 23, 1984, abandoned.

This invention relates to a process for producing 2,6-naphthalenedicarboxylic acid by oxidizing 2,6-diisopropylnaphthalene or its oxidation product with molecular oxygen. More specifically, it relates to a process for producing 2,6-naphthalenedicarboxylic acid by performing the aforesaid oxidation in a solvent containing an aliphatic monocarboxylic acid in the presence of a large amount of a catalyst containing a heavy metal element and bromine element.

2,6-Naphthalenedicarboxylic acid (to be sometimes abbreviated as "2,6-NDA" hereinafter) or its derivatives such as an ester or an acid chloride is a compound valuable as a dibasic acid component of various polyesters and polyamides. Particularly, poly(ethylene 2,6-naphthalate) prepared from 2,6-NDA and ethylene glycol has better heat resistance and mechanical properties than polyethylene terephthalate, and is useful as a polymer giving films or textile products.

A known conventional process for producing 2,6-NDA comprises the oxidation reaction of 2,6-dimethylnaphthalene, for example, oxidizing 2,6-dimethylnaphthalene with molecular oxygen in an acetic acid solvent in the presence of a catalsyt composed of cobalt element, manganese element and bromine element. According to this process, the oxidation of 2,6-dimethylnaphthalene to 2,6-NDA is relatively easy, and the desired 2,6-NDA of a relatively high purity can be obtained in a high yield.

The method of producing the starting 2,6-dimethylnaphthalene in this process, however, is complex, and this compound of high purity or quality is difficult to obtain in quantities at low costs. Known methods for producing 2,6-dimethylnaphthalene include, for example, methylation of naphthalene, isomerization of dimethylnaphthalene, disproportionation of monomethylnaphthalene, and transalkylation. All of these methods are not free from the formation of other isomers than 2,6-dimethylnaphthalene, particularly 2,7-dimethylnaphthalene, and the isolation of 2,6-dimethylnaphthalene from the mixed dimethylnaphthalenes is extremely difficult because 2,6-dimethylnaphthalene and 2,7-dimethylnaphthalene have very close melting and boiling points and very similar dissolving characteristics.

2,6-NDA obtained by the oxidation of 2,6-dimethylnaphthalene containng 2,7-dimethylnaphthalene gives a polymer such as polyethylene naphthalate having lower heat resistance or mechanical properties than a polymer obtained from highly pure 2,6-NDA.

In contrast, diisopropylnaphthalene can be easily synthesized by alkylation of naphthalene with propylene (isopropylation). This alkylation reaction is very easy, and the resulting alkylation product, as required, can be easily disproportionated, isomerized or transalkylated to give a reaction product having a high 2,6-diisopropylnaphthalene content. The separation of 2,6-diisopropylnaphthalene from the resulting reaction product is also very easy.

Investigations of the present inventors, however, have shown that when 2,6-diisopropylnaphthalene (to be sometimes abbreviated "2,6-DIPN" hereinafter) is oxidized under known reaction conditions suitable for the oxidation of p-xylene or 2,6-dimethylnaphthalene, the yield of 2,6-NDA is extremely low and since large amounts of by-products are formed, the purity of the resulting 2,6-NDA is low. For this reason, it has been found impossible to obtain 2,6-NDA from 2,6-DIPN industrially by employing known reaction conditions for oxidizing p-xylene or 2,6-dimethylnaphthalene (see Comparative Example 1 given hereinafter).

When various alkyl-substituted aromatic hydrocarbons, especially alkyl-substituted naphthalenes typified by dimethylnaphthalene are oxidized by a process involving using a catalyst composed of a heavy metal element such as cobalt or manganese and bromine element and an aliphatic monocarboxylic acid solvent, the yield of the desired product is low or its purity is low. It is known that in such a case, the following two methods are employed as measures for improving this process.

One is a so-called multistep temperature elevating reaction method in which the oxidation reaction is divided into a multiplicity of steps and the reaction temperature is elevated from a low one in the early stage of the reaction stepwise or continuously until the reaction is completed. For example, Japanese Laid-Open Patent Publication No. 17,453/1977 and Japanese Patent Publication No. 13,495/1984 describe an example in which 2,6-dimethylnaphthalene was oxidized in two steps at a temperature of 100° and 190° C. respectively to give 2,6-NDA in a yield of 91% (when the oxidation is carried out in one step at 190° C., the yield of 2,6-NDA is 74%). However, if this multistep temperature elevating method is applied to the oxidation of 2,6-DIPN, the yield of the resulting 2,6-NDA is about 50% at the highest, and the method cannot be industrially feasible (see Comparative Example 2 given hereinbelow).

Another measure is a so-called low material concentration oxidation method in which the reaction is carried out while maintaining the concentration of the starting material in the solvent low. For example, Japanese Patent Publication No. 3,337/1981, Japanese Laid-Open Patent Publication No. 7,945/1977, and U.S. Pat. No. 3,870,754 describe that by using the low material concentration method in the oxidation of dimethylnaphthalene, NDA is obtained in a relatively high yield. Japanese Laid-Open Patent Publication No. 142,544/1975 describes that by using the low material concentration oxidation method in the oxidation of acenaphthene, NDA can be obtained in a relatively high yield. However, even if such a low material concentration oxidation method is applied to the oxidation of 2,6-DIPN, the yield of 2,6-NDA is still far from being industrially satisfactory (see Comparative Examples 3, 4, 5 and 6 given hereinafter).

Thus, the production of 2,6-NDA by the oxidation of 2,6-DIPN cannot give favorable results even by using known conditions for an oxidation reaction using a heavy metal and bromine, which has been regarded as the most powerful oxidizing method in the oxidation of alkyl aromatic hydrocarbons.

Accordingly, no attention has previously been paid to the industrial production of 2,6-NDA from 2,6-DIPN.

It is an object of this invention to provide a novel process for producing 2,6-naphthalenedicarboxylic acid from 2,6-diisopropylnaphthalene.

Another object of this invention is to provide a process for producing 2,6-naphthalenedicarboxylic acid in a high yield from 2,6-diisopropylnaphthalene which can be obtained easily in high purity.

Still another object of this invention is to provide a process for producing highly pure 2,6-naphthalenedicarboxylic acid in a high yield from 2,6-diisopropylnaphthalene while inhibiting side reactions.

Yet another object of this invention is to provide novel oxidation reaction conditions for achieving the aforesaid objects in the production of 2,6-naphthalenedicarboxylic acid from 2,6-diisopropylnaphthalene, particularly the very large amount of the catalyst based on 2,6-diisopropylnaphthalene and various novel oxidation reaction conditions relating to it.

A further object of this invention is to provide a process for producing 2,6-naphthalenedicarboxylic acid in accordance with the aforessaid objects from an oxidation product of 2,6-diisopropylnaphthalene.

Further objects and advatanges of this invention will become apparent from the following description.

According to this invention, these objects and advantages of the invention are achieved by a process for producing 2,6-naphthalenedicarboxylic acid which comprises oxidizing 2,6-diisopropylnaphthalene or its oxidation product with molecular oxygen in a reaction medium containing at least 50% by weight of an aliphatic monocarboxylic acid having not more than 3 carbon atoms in the presence of an oxidation catalyst comprising (A) at least one heavy metal element selected from the group consisting of cobalt and manganese, and (B) bromine element, the 2,6-diisopropylnaphthalene and/or its oxidation product being used in a proportion of 0.1 to 5 moles per gram-atom of the heavy metal element of the oxidation catalyst.

In the process of this invention, the starting material is 2,6-diisopropylnaphthalene (2,6-DIPN for short) or its oxidation product.

The oxidation product of 2,6-DIPN is formed by the oxidation of 2,6-DIPN either separately or in situ and finally gives the desired 2,6-NDA. Preferably, the starting material of this invention is represented by the following general formula (I).

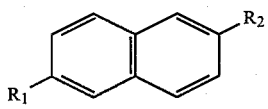

(1)

wherein $R_1$ is a group selected from the class consisting of

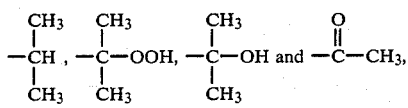

and $R_2$ is a group selected from the class consisting of the same groups $R_1$ as above, —COOH and —CHO and may be the same as or different from $R_1$.

Preferred starting materials are those of formula (I) in which $R_1$ and $R_2$ are identical or different and selected from

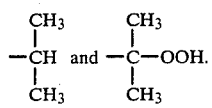

The oxidation catalyst used in this invention comprises (A) at least one heavy metal selected from the group consisting of cobalt and manganese elements (to be referred to as component A), and (B) bromine element (to be referred to as component B).

Components A and B may be in any form capable of being dissolved in the oxidation reaction system in accordance with this invention. Component A is usually in the form of a compound, and component B, in the form of a simple substance or a compound.

Examples of cobalt and manganese forming component A include their oxides; their hydroxides, their inorganic salts such as carbonates or halides, especially bromides; and their organic carboxylic acid salts such as formic acid, acetic acid, propionic acid, naphthenic acid or aromatic carboxylic acids, especially NDA. The bromides and the aliphatic carboxylic acid salts particularly the acetates are preferred.

Bromine forming component B may be in the form of any organic or inorganic compound which dissolves in the oxidation reaction system to generate a Br ion. Specific examples include molecular bromine ($Br_2$), inorganic bromine compounds such as hydrogen bromide and hydrobromides, and organic bromine compounds, for example alkyl bromides such as methyl bromide, ethyl bromide, bromoform and ethylene bromide, and brominated fatty acids such as bromoacetic acid and polybromoacetic acid. Preferred among them are molecular bromine, hydrogen bromide, sodium bromide, potassium bromide, lithium bromide, ammonium bromide, ethyl bromide, bromoacetic acid, cobalt bromide and manganese bromide.

It is important that in the process of this invention, component A should be used in an amount very large for 2,6-DIPN or its oxidation product to be oxidized. Investigations of the present inventors have shown that in contrast to the oxidation of alkyl-substituted aromatic hydrocarbons other than 2,6-DIPN such as 2,6-dimethylnaphthalene or p-xylene, the oxidation of 2,6-DIPN results in a very rapid formation of the oxidation intermediate in the early stage of the reaction, and despite this, the catalyst in the oxidation reaction mixture substantially loses activity, and that therefore, oxidation to the desired 2,6-DNA does not easily proceed sufficiently but rather side reactions are promoted.

In order to produce 2,6-NDA from 2,6-DIPN smoothly by oxidation, the present inventors furthered their investigations and found that when in the oxidation of 2,6-DIPN or its oxidation derivative to 2,6-NDA, the amount of cobalt element and/or manganese element (component A) in the oxidation catalyst used to oxidize 2,6-DIPN or its oxidation derivative is much larger than amounts known heretofore, the yield of the final 2,6-NDA is unexpectedly increased strikingly.

According to this invention, the heavy metal element as component A for oxidizing 1 mole of the starting 2,6-DIPN or its oxidation product is used in an amount of 0.2 to 10 gram-atoms. In other words, the starting 2,6-DIPN or its oxidation product is used in a proportion of 0.1 to 5 moles per gram-atom of the heavy metal element component A.

When the proportion of 2,6-DIPN or its oxidation product used exceeds 5 moles per gram-atom of the heavy metal element component A, the yield of 2,6-NDA tends to decrease abruptly. On the other hand, the use of the starting material in an amount of less than 0.1 mole brings about no industrial advantage and rather complicates the reaction operation or the posttreatment of the reaction mixture. Consequently, the productivity decreases, and the process becomes industrially disadvantageous.

The preferred proportion of the heavy metal element component A is 0.3 to 5.0 gram-atoms, especially 0.5 to 3.0 gram-atoms, per mole of the starting 2,6-DINP or its oxidation product.

Cobalt or manganese or both are used as component A of the oxidation catalyst. Manganese exhibits better activity than cobalt and is therefore preferred. A mixture of cobalt and manganese is the best catalyst used in this invention because it shows much higher activity than any of cobalt and manganese used singly.

When the mixture of cobalt and manganese is used as component A of the catalyst, the preferred mixing ratio varies depending upon the reaction temperature, the reaction time, the amount of the catalyst, the amount of the solvent, etc. Usually, the preferred Co:Mn atomic ratio is from 1:99 to 99:1, especially from 10:90 to 95:5.

A minor portion of bromine as component B of the oxidation catalyst may dissipate as a volatile compound during the reaction, or may be lost as a nuclearly brominated product which cannot easily be decomposed under the reaction conditions. However, a greater portion of it remains in the reaction system during the reaction and repeatedly exhibits its catalytic effect without being deactivated. In contrast to component A, therefore, bromine needs not to be used in a stoichiometrically large amount with regard to the starting material, nor is it necessary to use bromine in a large amount proportional to the amount of component A in the reaction system. Bromine is characteristic in that it can fully exhibit its catalytic effect even when used in a small amount.

The optimum concentration of bromine used in the reaction depends not only on the concentration of component A but also on other reaction conditions such as the reaction temperature, the concentration of the starting material and the amount of the solvent. The preferred concentration of bromine used in this invention is about 0.05 to 0.5 in terms of its atomic ratio to component A used. Bromine could be used in a larger proportion, for example, in an atomic ratio of up to 2, but even when it is used in such a large proportion, it exerts no substantial effect on the yield of 2,6-NDA.

At least 50% by weight, preferably at least 70% by weight, of the reaction medium used in the process of this invention may be an aliphatic monocarboxylic acid having not more than 3 carbon atoms. Examples of the aliphatic monocarboxylic acid are formic acid, acetic acid, propionic acid and bromoacetic acid. Acetic acid is most suitable. If required, the aliphatic monocarboxylic acid is used as a mixture with water or another medium. When it contains water, the proportion of water is desirably not more than 30% by weight, especially not more than 20% by weight.

Intrinsically, the reaction medium is used to dissolve the starting material and the catalyst at least partly and to facilitate contact of them with molecular oxygen. In addition, it promotes or facilitates the dispersion of heat, the removal of heat, the flowability of the reaction mixture, the crystal growth of the reaction product, etc., and thus makes it easy to practice the process of this invention industrially.

The amount of the reaction medium should therefore be determined according to the respective purposes of use, and is not essentially restricted. In practice, the amount of the reaction medium is at least 2 times, preferably 2 to 20 times, more preferably 3 to 15 times, especially preferably 3 to 10 times, the total weight of the starting material, its oxidation intermediate and the desired 2,6-NDA in the reaction system.

If the amount of the reaction medium is too small, the objects of the present invention are not fully achieved, and the smooth proceeding of the reaction is hampered. Even if the reaction medium is used in a larger amount than that described above, the reaction itself is not promoted, but rather losses of the reaction medium by oxidation and combustion increase to disadvantage.

The process of this invention is performed by oxidizing 2,6-DIPN or its oxidation product with molecular oxygen in the aforesaid reaction medium in the presence of the oxidation catalyst.

The concentration of the starting 2,6-DIPN or its oxidation product in the reaction system based on the oxidation catalyst is maintained preferably at up to 0.2 mole, more preferably up to 0.1 mole, above all advantageously up to 0.05 mole, per gram-atom of the heavy metal element (component A) of the oxidation catalyst.

If the reaction is carried out while maintaining the concentration of the starting material based on component A at more than 0.2 mole, it is difficult to inhibit occurrence of side-reactions due to the rapid progress of the reaction even if the starting material is used in a proportion of 0.1 to 5 moles per gram of component A. Consequently, the yield of the desired 2,6-NDA tends to decrease.

However, generally in a continuous reaction or at least in a semi-batch reaction, the disappearance of the starting material by reaction is rapid so long as the reaction temperature and the concentration of oxygen (partial pressure of oxygen) are maintained within preferred conditions. Thus, it is comparatively easy to maintain the concentration of the starting material during the reaction at not more than 0.2 mole.

Advantageously, the reaction medium is used in such a proportion that the concentration of the heavy metal element (component A) of the oxidation catalyst in the reaction medium is at least 1% by weight, preferably 1.2 to 25% by weight, more preferably 2 to 20% by weight, based on the reaction medium. If the reaction medium is used in such a proportion that the concentration of component A is less than 1% by weight, the yield of 2,6-NDA tends to decrease.

Pure oxygen or a gaseous mixture of it with a diluting inert gas may be used as a source of molecular oxygen used in the process of this invention. For practical purposes, air is the most easily obtainable gas containing molecular oxygen. Air may be used as such or if required as concentrated or diluted with oxygen or an inert gas.

The oxidation reaction in the process of this invention is possible under normal atmospheric pressure, but is accelerated under elevated pressures.

Generally, the reaction proceeds more rapidly as the partial pressure of oxygen in the reaction system is higher. From a practical standpoint, the partial pressure of oxygen is sufficiently at least 0.1 kg/cm$^2$-abs., preferably at least 0.2 kg/cm$^2$-abs., for example about 0.1 8 kg/cm$^2$-abs. Even when the total pressure of a gaseous mixture of oxygen with an inert gas is not more than 30 kg/cm$^2$-G, the reaction rapidly proceeds to give 2,6-NDA in a high yield.

The reaction is carried out preferably at a temperature of 140° to 210° C., more preferably 160° to 200° C. The reaction proceeds even at 60° C., and can be practiced at temperatures of up to 220° C. At less than 60° C., the reaction rate is too slow, and at temperatures above 220° C., proportion of by-products formed increases to decrease the yield of 2,6-NDA.

In performing the oxidation reaction of the process of this invention, the oxidation catalyst, the reaction medium and the starting material are fed into a reactor (as required, after heating) simultaneously or separately or with the lapse of time. A gas containing molecular oxygen is blown into the reactor, and while maintaining a predetermined pressure and temperature, the reaction is carried out for a sufficient period of time until the desired 2,6-NDA is obtained.

As the reaction proceeds, molecular oxygen is absorbed to generate a large amount of the heat of reaction. Usually, therefore, external warming or heating during the oxidation reaction is unnecessary. Rather, it is preferred to remove the heat and maintain the predetermined reaction temperature.

The removal of heat can be easily effected by known methods, for example by an internal heat removing method wherein the reaction medium such as acetic acid or water is evaporated or the blown gas is released to entrain the heat, or by an external method in which the reaction system is cooled by externally applying a cooling medium such as water or steam, or by using both of these methods.

When the starting material in the reaction system disappears and the end of the reaction draws near, absorption of molecular oxygen almost ceases apparently. The reaction is terminated at this point.

The separation and recovery of 2,6-NDA from the reaction mixture after the reaction, the purification of the recovered 2,6-NDA, the after-treatment, recycling and re-use of the mother liquor left after separation of 2,6-NDA may be carried out by customary procedures used in the production of 2,6-NDA from other starting materials such as 2,6-dimethylnaphthalene or in the production of terephthalic acid from p-xylene.

When the reaction has been terminated, the presence of a reaction intermediate not completely converted to 2,6-NDA may sometimes be seen to be present in the reaction mixture. In such a case, the reaction mixture is further contacted with molecular oxygen (post-oxidation) to complete the reaction. Consequently, the yield of 2,6-NDA can be increased, and at the same time, the unwanted byproducts or their intermediates are oxidatively decomposed to increase the purity of the resulting 2,6-NDA.

The post-oxidation can be carried out in the oxidation reaction vessel in which the main oxidation reaction has been carried out. Alternatively, after the main oxidation reaction, the reaction mixture is first transferred to a separate vessel, and then it is contacted with molecular oxygen for a required period of time. The reaction pressure and temperature of post-oxidation need not to be the same as those of the main reaction, and may be higher or lower.

The after-treatment of the reaction mixture obtained by post-oxidation, for example the separation and recovery of 2,6-NDA, may be carried out in the same way as described above.

The process of this invention may be carried out batchwise, semi-continuously or continuously.

Advantageously, the process of this invention is carried out continuously or semicontinuously because the concentration of the starting material in the oxidation reaction can be easily maintained low.

Hence, according to this invention, there is provided a process for producing 2,6-naphthalenedicarboxylic acid which comprises oxidizing 2,6-diisopropylnaphthalene or its oxidation product as a starting material with molecular oxygen in a reaction medium containing at least 50% by weight of an aliphatic monocarboxylic acid having not more than 3 carbon atoms in the presence of an oxidation catalyst comprising (A) at least one heavy metal element selected from t-he group consisting of cobalt and manganese and (B) bromine element, wherein 2,6-diisopropylnaphthalene and/or its oxidation product is continuously or semicontinuously added to the reaction system so that it is used in a proportion of 0.1 to 5 moles per gram-atom of the heavy metal element of the oxidation catalyst, the reaction mixture containing the resulting 2,6-naphthalenedicarboxylic acid is partly or wholly withdrawn from the reaction system, 2,6-naphthalenedicarboxylic acid is separated from the reaction mixture, and the mother liquor is recycled to the oxidation reaction either as such or after, as required, water is removed therefrom.

The starting 2,6-DIPN or its oxidation product can be added to the reaction system continuously or semicontinuously (in several portions with the lapse of time). Withdrawal of part of the reaction mixture may be effected contiuously or semicontinuously. The withdrawal of the whole reaction mixture may be carried out at a time.

The oxidation catalyst may be caused to be present in advance in a required amount in the reaction system, or may be added to it continuously or semicontinuously during the reaction.

The reaction mixture withdrawn from the reaction system may be subjected, as required, to the post-oxidation described above, and 2,6-naphthalenedicarboxylic acid is separated. The whole or a part of the mother liquor, either as such or after optionally removing water therefrom, can be again used in the oxidation reaction.

According to the process of this invention, 2,6-NDA obtained heretofore only in a low yield from 2,6-DIPN or its oxidation product can be obtained easily in a high purity and yield. The process of this invention can provide 2,6-NDA of high quality at lower costs than any prior process can.

2,6-NDA obtained by the process of this invention is used, for example, as a raw material for polyesters and polyamides and gives polymers of high quality.

The following examples illustrate the process of this invention. All parts in these examples are by weight.

COMPARATIVE EXAMPLE 1

A titanium-lined autoclave equipped with a reflux condenser, a gas blowing tube, a discharge tube and a stirrer was charged simultaneously with 2,670 parts of 2,6-diisopropylnaphthalene (2,6-DIPN), 13,350 parts of glacial acetic acid (AcOH), 48 parts of cobalt acetate tetrahydrate [Co(OAc)$_2$.4H$_2$O], 95 parts of manganese acetate tetrahydrate [Mn(OAc)$_2$.4H$_2$O] and 5.7 parts of ammonium bromide (NH$_4$Br). The Co+Mn/2,6-DIPN mole ratio was 0.046, and Co+Mn/AcOH was 0.24% by weight. While the reaction system was maintained at a temperature of 180° C. and a pressure of 30 kg/cm$^2$-G, compressed air was passed into the autoclave at an oxygen introducing rate of 80 parts/min. with vigorous stirring, and the reaction was carried out for 3 hours.

After the reaction, the reaction product was analyzed. There remained 180 parts of the starting 2,6-DIPN, and 1,106 parts of 2,6-naphthalenedicarboxylic acid (2,6-NDA) having a purity of 85.6% was obtained. This corresponds to a yield of 37.3 mole % based on the reacted 2,6-DIPN.

COMPARATIVE EXAMPLE 2

The same reactor as in Comparative Example 1 was charged simultaneously with 1,000 parts of 2,6-DIPN, 15,000 parts of glacial acetic acid, 72 parts of cobalt acetate tetrahydrate, 143 parts of manganese acetate tetrahydrate and 85 parts of ammonium bromide ($NH_4Br$). The Co+Mn/2,6-DIPN mole ratio was 0.185, and Co+Mn/AcOH was 0.33% by weight. While the reaction system was maintained at a temperature of 140° C. and a pressure of 30 kg/cm$^2$-G, compressed air was passed into the reactor at an oxygen introducing rate of 40 parts/min. with vigorous stirring, and the reaction was carried out for 1 hour. Then, the temperature of the reaction mixture was raised gradually to 200° C. over the course of 30 minutes, and then it was heated at 200° C. for 30 minutes.

During this time, compressed air was continuously passed into the reactor at an oxygen introducing rate of 30 parts/min. under a pressure of 30 kg/cm$^2$-G.

After the reaction, the reaction product was analyzed. The starting 2,6-DIPN all disappeared, and 495 parts of 2,6-NDA was obtained. This corresponds to a yield of 48.6 mole %.

EXAMPLE 1

A titanium-lined pressure reactor equipped with a reflux condednser, a gas blowing tube, a discharge tube, a pump for continuous introduction of the starting material and a stirrer was charged with 8,274 parts of glacial acetic acid, 274 parts of cobalt acetate tetrahydrate, 539 parts of manganese acetate tetrahydrate and 35 parts of lithium bromide monohydrate ($LiBr \cdot H_2O$). Co+Mn/AcOH was 2.17% by weight. While the reaction system was maintained at a temperature of 200° C. and a pressure of 30 kg/cm$^2$-G, 1,172 parts of 2,6-DIPN was continuously fed into the reactor at a rate of 19.5 parts/min. for 1 hour and simultaneously compressed air was passed into it at an oxygen introducing rate of 40 parts/min. The Co+Mn/2,6-DIPN mole ratio was 0.598.

The reaction immediately began, and the absorption of oxygen was observed. When the feeding of 2,6-DIPN was terminated in 1 hour, the absoprtion of oxygen was hardly observed.

The reaction mixture was maintained at 200° C. and 30 kg/cm$^2$-G for 2 hours and the passing of air was continued to complete the reaction. The reaction product was taken out, and a solid precipitate composed mainly of 2,6-NDA was separated by filtration.

· The mother liquor composed mainly of the catalyst solution was recycled to the next oxidation reaction. The solid precipitate was washed, dried and analyzed. There was obtained 1,064 parts of 2,6-NDA having a purity of 93.0%.

The theoretical yield of the resulting 2,6-NDA based on the starting 2,6-DIPN was 82.5 mole %.

Only a trace of the starting 2,6-DIPN was observed in the reaction product immediately after stopping the feeding of the starting material It is assumed from this that the 2,6-DIPN/Co+Mn mole ratio in the reaction system during the reaction was maintained at less than 0.01.

COMPARATIVE EXAMPLE 3

The procedure of Example 1 was repeated except that Co+Mn/2,6-DIPN mole ratio=0.146, (Co:Mn:Br=1:2:0.3), and Co+Mn/AcOH=0.53% by weight. There was obtained 2,6-NDA having a purity of 87.0% only in a yield of 54.4 mole %.

EXAMPLE 2

The same reactor as used in Example 1 was charged with 8,721 parts of glacial acetic acid, 955 parts of cobalt acetate tetrahydrate, 1,880 parts of manganese acetate tetrahydrate and 122 parts of lithium bromide monohydrate. Co+Mn/AcOH was 7.43% by weight. While the reaction system was maintained at a temperature of 160° C. and a pressure of 30 kg/cm$^2$-G, 1,176 parts of 2,6-DIPN was added continuously at a rate of 19.6 parts/min. for 1 hour with vigorous stirring. The Co+Mn/2,6-DIPN mole ratio was 2.077. At the same time, compressed air was passed into the reactor at an oyxgen introducing rate of 40 parts/min. After the feeding of 2,6-DIPN, the passing of air was continued at 160° C. and 30 kg/cm$^2$-G for 2 hours to terminate reaction.

In the reaction product, there was formed 1,086 parts of 2,6-NDA having a purity of 93.6% as a solid. This corresponds to a yield of 84.9 mole % based on the starting 2,6-DIPN.

The starting 2,6-DIPN remained only in an amount of 3.04% based on the total amount fed in the reaction product immediately after stopping the feeding of the starting material. It was assumed therefore that the 2,6-DIPN/Co+Mn mole ratio in the reaction system during the reaction was maintained at not more than 0.02.

COMPARATIVE EXAMPLE 4

The procedure of Example 2 was repeated except that the reaction was carried out while maintaining the Co+Mn/2,6-DIPN mole ratio at 0.144, and Co+Mn/AcOH at 0.51% by weight, (Co:Mn:Br at 1:2:0.3). The yield of the resulting 2,6-NDA was 50.2 mole %.

EXAMPLES 3–7 AND COMPARATIVE EXAMPLES 5–6

Similarly to Example 1, 2,505 parts of 2,6-DIPN was fed at a rate of 41.8 parts/min. into a mixture of 16,884 parts of glacial acetic acid, 3,817 parts of cobalt acetate tetrahydrate, 7,512 parts of manganese acetate tetrahydrate and 482 parts of lithium bromide monohydrate (Co+Mn/2,6-DIPN mole ratio=3.897; Co+Mn/AcOH=15.33% by weight). While maintaining the reaction system at a temperature of 180° C. and a pressure of 30 kg/cm$^2$-G, compressed air was fed into the reaction mixture at an oxygen introducing rate of 80 parts/min. for 1 hour, and then post oxidation was carried out for 2 hours.

As a result of the reaction, 2,339 parts of 2,6-NDA having a purity of nearly 100% was obtained. This corresponds to a yield of 91.7%.

In the reaction product immediately after stopping of feeding of the starting material, the amount of the remaining starting 2,6-DIPN was only 0.65% based on the total amount fed. It was assumed from this that the mole ratio of 2,6-DIPN/(Co+Mn) in the reaction system during the reaction was maintained at not more than 0.002.

The same reaction as above was carried out without changing the Co:Mn:Br ratio but with varying amounts of the catalyst and at varying stoichiometrical ratios of Co+Mn/2,6-DIPN. The results are shown in Table 1.

A marked difference in the yield of 2,6-NDA was observed between both sides of Co+Mn/2,6-DIPN=0.2 as a border.

TABLE 1

| Run | Co + Mn/ 2,6-DIPN mole ratio | Co + Mn/AcOH (% by weight) | Yield of 2,6-NDA (mole %) |
|---|---|---|---|
| Example 3 | 3.897 | 15.33 | 91.7 |
| Example 4 | 1.905 | 7.50 | 88.2 |
| Example 5 | 1.099 | 4.32 | 85.6 |
| Example 6 | 0.557 | 2.19 | 79.0 |
| Example 7 | 0.281 | 1.11 | 71.5 |
| Comparative Example 5 | 0.141 | 0.55 | 51.1 |
| Comparative Example 6 | 0.036 | 0.14 | 26.5 |

In Examples 4 to 7, the amount of the remaining starting 2,6-DIPN in the reaction system was only 0.2 to 1.0% based on the total amount of the starting material fed. It was concluded from this that the 2,6-DIPN-/Co+Mn mole ratio in the reaction system during the reaction was in the range of from 0.002 to 0.03.

EXAMPLE 8

The same reactor as used in Example 1 was charged with 16,844 parts of glacial acetic acid, 3,287 parts of cobalt acetate tetrahydrate and 136 parts of sodium bromide. Co/AcOH was 4.62% by weight. While the reaction system was maintained at a temperature of 160° C. and a pressure of 30 kg/cm$^2$-G, 2,491 parts of 2,6-DIPN was fed continuously for one hour at a rate of 41.5 parts/min. with vigorous stirring and simultaneously compressed air was psassed into the reactor at a rate of 80 parts/min. The Co/2,6-DIPN mole ratio was 1.125. After the termination of feeding of 2,6-DIPN, the passing of the air was continued for 2 hours at 160° C. and 30 kg/cm$^2$ to complete the reaction.

There was obtained 1,783 parts of 2,6-NDA having a purity of 92.2% as a solid in the reaction product. This corresponds to a yield of 64.8 mole % based on the starting 2,6-DIPN.

COMPARATIVE EXAMPLE 7

The procedure of Example 8 was carried out except that Co/2,6-DIPN mole ratio=0.150, and Co/AcOH=0.62% by weight, (Co:Br=1:0.1). The yield of 2,6-NDA was 40.5 mole %.

EXAMPLE 9

The same reactor as used in Example 1 was charged with 16,772 parts of glacial acetic acid, 3,235 parts of manganese acetate tetrahydrate and 136 parts of sodium bromide. Mn/AcOH was 4.57% by weight. While the reaction system was maintained at a temperature of 180° C. and a pressure of 30 kg/cm$^2$-G, 2,454 parts of 2,6-DIPN was continuously fed for 1 hour at a rate of 40.9 parts with vigorous stirring and simultaneously compressed air was passed into the reactor at an oxygen introducing rate of 80 parts/min. The Mn/2,6-DIPN mole ratio was 1.142. After the end of feeding of 2,6-DIPN, the passing of air was continued further for 2 hours at 180° C. and 30 kg/cm$^2$-G to complete the reaction.

There was formed 2,005 parts of 2,6-NDA having a purity of 94.1% as a solid in the reaction product. This corresponds to a yield of 75.5 mole % based on the starting 2,6-DIPN.

COMPARATIVE EXAMPLE 8

The procedure of Example 9 was repeated except that the reaction was carried out while maintaining the Mn/2,6-DIPN mole ratio at 0.150, and Mn/AcOH at 0.60% by weight, (Mn:Br at 1:0.1). The yield of the resulting 2,6-NDA was 51.0 mole %.

EXAMPLE 10

A titanium-lined autoclave equipped with a reflux condenser, a gas blowing tube, a discharge tube and a stirrer was charged simultaneously with 333 parts of 2,6-DIPN, 15,000 parts of glacial acetic acid, 433 parts of cobalt acetate tetrahydrate, 853 parts of manganese acetate tetrahydrate and 85 parts of ammonium bromide. The Co+Mn/ 2,6-DIPN mole ratio was 3.328, and Co+Mn/AcOH was 1.96% by weight. While the reaction system was maintained at a temperature of 160° C. and a pressure of 30 kg/cm$^2$-G, compressed air was passed into the autoclave at an oxygen introducing rate of 40 parts/min. for 3 hours with vigorous stirring.

After the reaction, the reaction product was analyzed. Most of the starting 2,6-DIPN disappeared, and 271 parts of 2,6-NDA having a purity of 96.1% was obtained. This corresponds to a yield of 76.7 mole % based on the starting 2,6-DIPN.

EXAMPLE 11

The same reactor as used in Example 10 was charged simultaneously with 333 parts of 2,6-DIPN, 15,000 parts of glacial acetic acid, 290 parts of cobalt acetate tetrahydrate, 569 parts of manganese acetate tetrahydrate and 87 parts of ammonium bromide. The Co+Mn/2,6-DIPN mole ratio was 2.224, and Co+Mn/AcOH was 1.31% by weight. The reaction was carried out by the same operation as in Example 10.

After the reaction, the reaction product was analyzed. There was obtained 255 parts of 2,6-NDA having a purity of 98.6%. This corresponds to a yield of 74.2 mole %.

EXAMPLE 12

A titanium-lined pressure reactor equipped with a reflux condenser, a gas blowing tube, a discharge tube, a pump for continuous introduction of the starting material and a stirrer was charged with 8,420 parts of glacial acetic acid, 137 parts of cobalt acetate tetrahydrate, 269 parts of manganese acetate tetrahydrate and 17 parts of lithium bromide monohydrate. Co+Mn/AcOH was 1.10% by weight. While the reaction mixture was maintained at a temperature of 180° C. and a pressure of 30 kg/cm$^2$-G, 1,247 parts of 2,6-DIPN was continuously fed into the reactor for 1 hour at a rate of 20.8 parts/min. with vigorous stirring and simultaneously compressed air was passed into the reactor at an oxygen introducing rate of 40 parts/min. The Co+Mn/2,6-DIPN mole ratio was 0.282.

The reaction began upon the starting of feeding, and the absorption of oxygen was observed. When the feeding of 2,6-DIPN was terminated in 1 hour, the absorption of oxygen was hardly observed.

The reaction mixture was further maintained at 180° C. and 30 kg/cm$^2$-G for 2 hours and the passing of air was continued to complete the reaction. The reaction product was taken out and analyzed. Most of the starting 2,6-DIPN disappeared, and 936 parts of 2,6-NDA having a purity of 97% by weight was obtained. This corresponds to a yield of 71.5 mole % based on the starting 2,6-DIPN.

EXAMPLE 13

The same reactor as used in Example 12 was charged with 16,958 parts of glacial acetic acid, 1,096 parts of cobalt acetate tetrahydrate, 2,156 parts of manganese acetate tetrahydrate and 140 parts of lithium bromide monohydrate. Co+Mn/AcOH was 4.38% by weight. While the reaction system was maintained at a temperature of 180° C. and a pressure of 30 kg/cm²-G, 2,550 parts of 2,6-DIPN was continuously fed for 1 hour at a rate of 42.5 parts/min. with vigorous stirring, and simultaneously compressed air was passed into the reactor at an oxygen introducing rate of 80 parts/min. The Co+Mn/2,6-DIPN mole ratio was 1.099.

After the end of feeding of 2,6-DIPN, the passing of air was continued for 2 hours at 180° C. and 30 kg/cm²-G to complete the reaction. The reaction product was taken out, and analyzed. The yield of 2,6-NDA was 85.6 mole %.

EXAMPLE 14

The same reactor as used in Example 12 was charged with 16,902 parts of glacial acetic acid, 3,816 parts of cobalt acetate tetrahydrate, 7,510 parts of mnganese acetate tetrahydrate and 473 parts of sodium bromide. Co+Mn/AcOH was 15.31% by weight. While the reaction system was maintained at a temperature of 180° C. and a pressure of 20 kg/cm²-G, 2,519 parts of 2,6-DIPN was fed continuously for 2 hours at a rate of 21.0 parts/min. and simultaneously compressed air was passed into the reactor at an oxygen introducing rate of 65 parts/min. The Co+Mn/2,6-DIPN mole ratio was 3.875.

After the end of feeding 2,6-DIPN, the passing of air was continued for 2 hours at 180° C. and 20 kg/cm²-G to complete the reaction. The reaction product was taken out and analyzed. The yield of 2,6-NDA was 90.8 mole %.

EXAMPLE 15

The same reactor as used in Example 12 was charged with 16,971 parts of glacial acetic acid, 1,089 parts of cobalt acetate tetrahydrate, 3,215 parts of manganese acetate tetrahydrate and 128 parts of ammonium bromide. Co+Mn/AcOH was 5.76% by wight. While the reaction mixture was maintained at a temperature of 200° C. and a pressure of 20 kg/cm²-G, 2,552 parts of 2,6-DIPN was continuously fed for 2 hours at a rate of 21.3 parts/min. with vigorous stirring, and simultaneously compressed air was passed into the reactor at an oxygen introducing rate of 80 parts/min. The Co+Mn/2,6-DIPN mole ratio was 1.454.

After the end of feeding of 2,6-DIPN, the passing of air was continued for 2 hours at 200° C. and 20 kg/cm²-G to complete the reaction. The reaction product was taken out, and a solid precipitate composed of 2,6-NDA was separated by filtration.

The mother liquor composed mainly of the catalyst solution was recycled to the next oxidation reaction. The solid precipitate was washed, dried and analyzed. There was obtained 2,248 parts of 2,6-NDA. Its theoretical yield based on the starting 2,6-DIPN was 86.55 mole %.

What is claimed is:

1. A process for producing 2,6-naphthalene-dicarboxylic acid which comprises oxidizing 2,6-diisopropylnaphthalene, its oxidation product, or mixtures thereof, as a starting material with molecular oxygen in a reaction medium containing at least 50% by weight of an aliphatic monocarboxylic acid having not more than three carbon atoms in the presence of an oxidation catalyst comprising (A) at least one heavy metal element selected from the group consisting of cobalt and manganese and (B) bromine element, wherein 2,6-diisopropylnaphthalene and/or its oxidation product is continuously or semi-continuously added to the reaction system so that it is used in a proportion of 0.1 to 5 moles per gram-atom of the heavy metal element of the oxidation catalyst, the starting material concentration within the reaction mixture being maintained during the oxidation reaction at up to 0.2 mole per gram-atom of the heavy metal element, the reaction mixture containing the resulting 2,6-naphthalene-dicarboxylic acid is partly or wholly withdrawn from the reaction system, 2,6-naphthalene-dicarboxylic acid is separated from the reaction mixture, and the mother liquor is recycled to the oxidation reaction either as such or after, as required, water is removed therefrom.

2. The process of claim 1 wherein the oxidation is carried out at a temperature of 140° to 210° C.

3. The process of claim 1 wherein the oxidation is carried out under an oxygen partial pressure of 0.1 to 8 kg/cm²-abs.

4. The process of claim 1 wherein the aliphatic monocarboxylic acid in the reaction medium is formic acid, acetic acid or propionic acid.

5. The process of claim 1 wherein the reaction medium consists essentially of the aliphatic monocarboxylic acid having not more than 3 carbon atoms and water.

6. The process of claim 1 wherein the reaction medium contains up to 30% by weight of water.

7. The process of claim 1 wherein the reaction medium is used in such a proportion that the concentration of the heavy metal element of the oxidation catalyst in the reaction medium in the reaction system is at least 1% by weight.

8. The process of claim 1 wherein the reaction medium is used in an amount at least 2 times the total weight of the starting material, its oxidation product and 2,6-naphthalenedicarboxylic acid present in the reaction system.

9. The process of claim 1 wherein 2,6-diisopropylnaphthalene or its oxidation product is represented by the following formula (I)

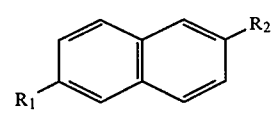

wherein R₁ is

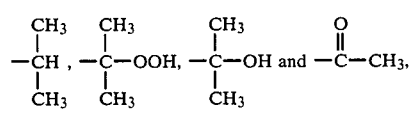

and R₂ is the same as R₁ or —CHO or —COOH.

10. The process of claim 9 wherein $R_1$ and $R_2$ are identical or different and are selected from the group consisting of

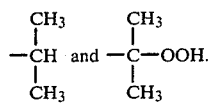

11. The process of claim 1 wherein the heavy metal element (A) of the oxidation catalyst is a mixture of cobalt and manganese at a Co:Mn atomic ratio of from 10:90 to 95:5.

12. A process for producing 2,6-naphthalenedicarboxylic acid which comprises oxidizing 2,6-diisopropylnaphthalene as a starting material with molecular oxygen in a reaction medium containing at least 50% by weight of an aliphatic monocarboxylic acid having not more than 3 carbon atoms in the presence of an oxidation catalyst comprising (A) at least one heavy metal element selected from the group consisting of cobalt and manganese, and (B) bromine element, the 2,6-diisopropylnaphthalene being used in a proportion of 0.1 to 5 moles per gram-atom of the heavy metal element of the oxidation catalyst and the starting material concentration within the reaction mixture being maintained during the oxidation reaction at up to 0.2 mole per gram-atom of the heavy metal element.

* * * * *